US012648688B2

(12) United States Patent
Wada et al.

(10) Patent No.: US 12,648,688 B2
(45) Date of Patent: Jun. 9, 2026

(54) MEDICAL SYSTEM AND MEDICAL METHOD

(71) Applicants: RIKEN, Saitama (JP); Topcon Corporation, Tokyo (JP)

(72) Inventors: Satoshi Wada, Wako (JP); Masayuki Maruyama, Wako (JP); Norihito Saito, Wako (JP); Kei Taneishi, Wako (JP); Yasufumi Fukuma, Wako (JP); Masahiro Akiba, Toda (JP); Gaku Takeuchi, Tokyo (JP); Kana Minamide, Tokyo (JP)

(73) Assignees: RIKEN, Wako (JP); TOPCON CORPORATION, Tokyo (JP)

( * ) Notice: Subject to any disclaimer, the term of this patent is extended or adjusted under 35 U.S.C. 154(b) by 685 days.

(21) Appl. No.: 17/921,645

(22) PCT Filed: Apr. 21, 2021

(86) PCT No.: PCT/JP2021/016178
§ 371 (c)(1),
(2) Date: Oct. 27, 2022

(87) PCT Pub. No.: WO2021/220910
PCT Pub. Date: Nov. 4, 2021

(65) Prior Publication Data
US 2023/0165456 A1 Jun. 1, 2023

(30) Foreign Application Priority Data
Apr. 30, 2020 (JP) ................................. 2020-080066

(51) Int. Cl.
*A61B 3/00* (2006.01)
*A61B 3/12* (2006.01)
*G16H 50/20* (2018.01)

(52) U.S. Cl.
CPC .......... *A61B 3/0025* (2013.01); *A61B 3/1233* (2013.01); *A61B 3/1241* (2013.01); *G16H 50/20* (2018.01)

(58) Field of Classification Search
CPC ......... A61B 3/0025; A61B 3/102; A61B 3/12; A61B 3/1233; A61B 3/1241; A61B 3/135;
(Continued)

(56) References Cited

U.S. PATENT DOCUMENTS 9,224,180 B2 12/2015 Macoviak et al.
10,052,026 B1 8/2018 Tran
(Continued)

FOREIGN PATENT DOCUMENTS

CA 3 083 035 A1 4/2019
JP 10-328152 A 12/1998
(Continued)

OTHER PUBLICATIONS

Extended European Search Report issued Apr. 26, 2024, in corresponding European Patent Application No. 21795564.0, 8pp.
(Continued)

*Primary Examiner* — Jack Dinh
(74) *Attorney, Agent, or Firm* — XSENSUS LLP

(57) ABSTRACT

According to a medical system of an aspect example, an ophthalmic data acquiring unit includes at least one ophthalmic examination apparatus for acquiring ophthalmic data from a patient, and an internal medicine data acquiring unit includes at least one internal medicine examination apparatus for acquiring internal medicine data from the patient. An inference processor is configured to perform inference processing using a trained model constructed by machine learning using training data that includes ophthalmic data, internal medicine data, and diagnostic result data.
(Continued)

The inference processor generates inferred diagnostic data by performing the inference processing based at least on the ophthalmic data of the patient acquired by the ophthalmic data acquiring unit and the internal medicine data of the patient acquired by the internal medicine data acquiring unit. An output unit outputs a result of the inference processing performed by the inference processor.

9 Claims, 7 Drawing Sheets

(58) Field of Classification Search
CPC ......... A61B 5/01; A61B 5/0205; A61B 5/021; A61B 5/026; A61B 5/091; A61B 5/14551; A61B 5/318; A61B 5/4842; A61B 5/7267; A61B 7/04; G16H 40/67; G16H 50/20
See application file for complete search history.

(56) References Cited

U.S. PATENT DOCUMENTS

| | | | |
|---|---|---|---|
| 10,702,166 | B1 | 7/2020 | Freeman et al. |
| 2011/0172545 | A1 | 7/2011 | Grudic et al. |
| 2011/0201962 | A1 | 8/2011 | Grudic et al. |
| 2011/0282169 | A1 | 11/2011 | Grudic et al. |
| 2012/0041279 | A1 | 2/2012 | Freeman et al. |
| 2012/0330117 | A1 | 12/2012 | Grudic et al. |
| 2013/0023781 | A1 | 1/2013 | Freeman et al. |
| 2013/0245397 | A1 | 9/2013 | Grudic et al. |
| 2015/0065826 | A1 | 3/2015 | Mulligan et al. |
| 2015/0073723 | A1 | 3/2015 | Mulligan et al. |
| 2015/0141769 | A1 | 5/2015 | Mulligan et al. |
| 2016/0015284 | A1 | 1/2016 | Grudic et al. |
| 2016/0038042 | A1 | 2/2016 | Mulligan et al. |
| 2016/0038043 | A1 | 2/2016 | Mulligan et al. |
| 2016/0162786 | A1 | 6/2016 | Grudic et al. |
| 2016/0327779 | A1 | 11/2016 | Hillman |
| 2016/0354054 | A1 | 12/2016 | Minegishi et al. |
| 2016/0367186 | A1 | 12/2016 | Freeman et al. |
| 2016/0374625 | A1 | 12/2016 | Mulligan et al. |
| 2017/0281020 | A1 | 10/2017 | Mulligan et al. |
| 2017/0303799 | A1 | 10/2017 | Grudic et al. |
| 2017/0325695 | A1 | 11/2017 | Freeman et al. |
| 2018/0098739 | A1 | 4/2018 | Freeman et al. |
| 2018/0192868 | A1 | 7/2018 | Sakurada et al. |
| 2018/0280646 | A1 | 10/2018 | Freeman et al. |
| 2019/0196172 | A1 | 6/2019 | Hillman |
| 2019/0221313 | A1 | 7/2019 | Rim et al. |
| 2020/0085292 | A1 | 3/2020 | Fukuma et al. |
| 2020/0329977 | A1 | 10/2020 | Freeman et al. |
| 2021/0038075 | A1 | 2/2021 | Sakai et al. |
| 2021/0173195 | A1 | 6/2021 | Hillman |
| 2022/0058796 | A1 | 2/2022 | Vaghefi Rezaei |
| 2022/0248966 | A1 | 8/2022 | Freeman et al. |

FOREIGN PATENT DOCUMENTS

| | | |
|---|---|---|
| JP | 2002-153487 A | 5/2002 |
| JP | 2008-36095 A | 2/2008 |
| JP | 2008-154804 A | 7/2008 |
| JP | 2016-123605 A | 7/2016 |
| JP | 2017-198 A | 1/2017 |
| JP | 2017-504836 A | 2/2017 |
| JP | 2017-148577 A | 8/2017 |
| JP | 2017-534421 A | 11/2017 |
| JP | 2018-29964 A | 3/2018 |
| JP | 2018-38518 A | 3/2018 |
| JP | 2018-110687 A | 7/2018 |
| JP | 2019-111010 A | 7/2019 |
| JP | 2019-527117 A | 9/2019 |
| JP | 2019-213734 A | 12/2019 |
| JP | 2020-36835 A | 3/2020 |
| JP | 2020-44027 A | 3/2020 |
| JP | 2020-48730 A | 4/2020 |
| WO | 2018/075521 A2 | 4/2018 |
| WO | 2020/055272 A1 | 3/2020 |

OTHER PUBLICATIONS

International Search Report and Written Opinion mailed on Jun. 15, 2021, received for PCT Application PCT/JP2021/016178, filed on Apr. 21, 2021, 8 pages including English Translation.
Ayusawa, "Clinical course and features in acute stage of Kawasaki disease", Japanese Journal of Clinical Medicine, Nippon Rinshosha Co. Ltd., vol. 72, No. 9, Sep. 1, 2014, pp. 1563-1567 (12 pages including English Abstract).

Ophthalmic Data Acquiring Unit 10

Ophthalmic Examination Apparatus 11–k

Ophthalmic Measurement Apparatus 12–m

Ophthalmic Imaging Apparatus 13–n

Ophthalmic Measurement Apparatus 12—m

Ocular Blood Flow Measurement Apparatus 14—m₁

Ocular Refraction Measurement Apparatus 15—m₂

FIG. 4

Inference Processor 30

Trained Model 31—g

First Trained Model 32—$g_1$

Second Trained Model 33—$g_2$

Output Unit 4

Transmitter 41

1

MEDICAL SYSTEM AND MEDICAL METHOD

CROSS-REFERENCE TO RELATED APPLICATIONS

This application is a national stage (under 35 U.S.C. 371) of International Patent Application No. PCT/JP2021/016178, filed Apr. 21, 2021, claiming priority to Japanese Patent Application No. 2020-080066, filed Apr. 30, 2020, both of which are herein incorporated by reference in their entirety.

TECHNICAL FIELD

The present disclosure relates generally to a medical system and a medical method.

BACKGROUND OF THE INVENTION

Symptoms of a disease and signs of aggravation (exacerbation, worsening) of a disease are complex, and various techniques and technologies have been developed to detect them. For example, Patent Document 1 below discloses, as a technique or technology for automatically and non-invasively performing early diagnosis, real-time monitoring, and tracking of blood loss in resuscitation procedures using transfusion (fluid infusion), an invention to estimate bleeding probability by analyzing physiological data obtained from a patient using various kinds of sensors. In addition, Patent Document 2 below discloses, as a technique or technology for determining the risk of infection without using advanced medical knowledge, a technique or technology for determining the risk of infection on the basis of the presence or absence of abnormalities in arterial blood oxygen saturation, body temperature, and heart rate.

PATENT DOCUMENT 1: Japanese Unexamined Patent Application Publication (Translation of PCT Application) No. 2017-534421 (International Publication No. WO 2016/061542)

PATENT DOCUMENT 2: Japanese Unexamined Patent Application Publication No. 2016-123605

BRIEF SUMMARY OF THE INVENTION

One object of the present disclosure is to provide a novel technique or technology for detecting a symptom and/or a sign of aggravation with a high degree of precision.

A medical system according to some aspect examples includes: an ophthalmic data acquiring unit that includes at least one ophthalmic examination apparatus for acquiring ophthalmic data from a patient; an internal medicine data acquiring unit that includes at least one internal medicine examination apparatus for acquiring internal medicine data from the patient; an inference processor configured to perform inference processing using a trained model constructed by machine learning using training data that includes ophthalmic data, internal medicine data, and diagnostic result data; and an output unit configured to output a result of the inference processing performed by the inference processor, wherein the inference processor is configured to generate inferred diagnostic data by performing the inference processing based at least on the ophthalmic data of the patient acquired by the ophthalmic data acquiring unit and the internal medicine data of the patient acquired by the internal medicine data acquiring unit.

2

In the medical system according to some aspect examples, the at least one ophthalmic examination apparatus includes either one of or both an ophthalmic measurement apparatus for acquiring ocular characteristic data and an ophthalmic imaging apparatus for acquiring ocular image data, the ophthalmic data to be input into the inference processor includes either one of or both ocular characteristic data acquired from the patient by the ophthalmic measurement apparatus and ocular image data acquired from the patient by the ophthalmic imaging apparatus, and the trained model includes a first trained model constructed by machine learning using training data that includes diagnostic result data and either one of or both ocular characteristic data and ocular image data.

In the medical system according to some aspect examples, the ophthalmic measurement apparatus includes either one of or both an ocular blood flow measurement apparatus and an ocular refraction measurement apparatus.

In the medical system according to some aspect examples, the ocular blood flow measurement apparatus includes either one of or both an optical coherence tomography apparatus and a laser speckle flowgraphy apparatus.

In the medical system according to some aspect examples, the ophthalmic imaging apparatus includes any one or more of an optical coherence tomography apparatus, a fundus camera, a slit lamp microscope, and a surgical microscope.

In the medical system according to some aspect examples, the at least one internal medicine examination apparatus includes any one or more of an electronic stethoscope, a pulse oximeter, a blood flowmeter, a spirometer, an electrocardiogram meter, a blood pressure meter, and a thermometer, the electronic stethoscope being for acquiring auscultatory sound data, the pulse oximeter being for acquiring blood oxygen saturation data, the blood flowmeter being for acquiring either one of or both blood flow data and pulse data, the spirometer being for acquiring respiratory function data, the electrocardiogram meter being for acquiring either one of or both electrocardiogram data and heart rate data, the blood pressure meter being for acquiring either one of or both blood pressure data and pulse data, and the thermometer being for acquiring body temperature data, the internal medicine data to be input into the inference processor includes any one or more of: auscultatory sound data acquired from the patient by the electronic stethoscope, blood oxygen saturation data acquired from the patient by the pulse oximeter, either one of or both blood flow data and pulse data acquired from the patient by the blood flowmeter, respiratory function data acquired from the patient by the spirometer, either one of or both electrocardiogram data and heart rate data acquired from the patient by the electrocardiogram meter, either one of or both blood pressure data and pulse data acquired from the patient by the blood pressure meter, and body temperature data acquired from the patient by the thermometer, and the trained model includes a second trained model constructed by machine learning using training data that includes diagnostic result data and any one or more of auscultatory sound data, blood flow data, pulse data, respiratory function data, electrocardiogram data, heart rate data, blood pressure data, and body temperature data.

In the medical system according to some aspect examples, the output unit includes a transmitter configured to transmit a result of the inference processing to a doctor's computer terminal that is located remotely from both the ophthalmic data acquiring unit and the internal medicine data acquiring unit.

In the medical system according to some aspect examples, the inference processor performs one or more of: inference processing for calculating a probability that the patient has pneumonia; inference processing for calculating a probability that the patient has an infectious disease associated with pneumonia; inference processing for determining a severity of pneumonia in the patient; and inference processing for determining a severity of an infectious disease associated with pneumonia in the patient.

These aspect examples allow the precision of detection processing of disease symptoms and/or signs of aggravation to be improved.

BRIEF DESCRIPTION OF THE SEVERAL VIEWS OF THE DRAWING

FIG. 4 is a diagram illustrating an example of a configuration of a medical system according to an aspect example.

DETAILED DESCRIPTION OF THE INVENTION

Figure 1:
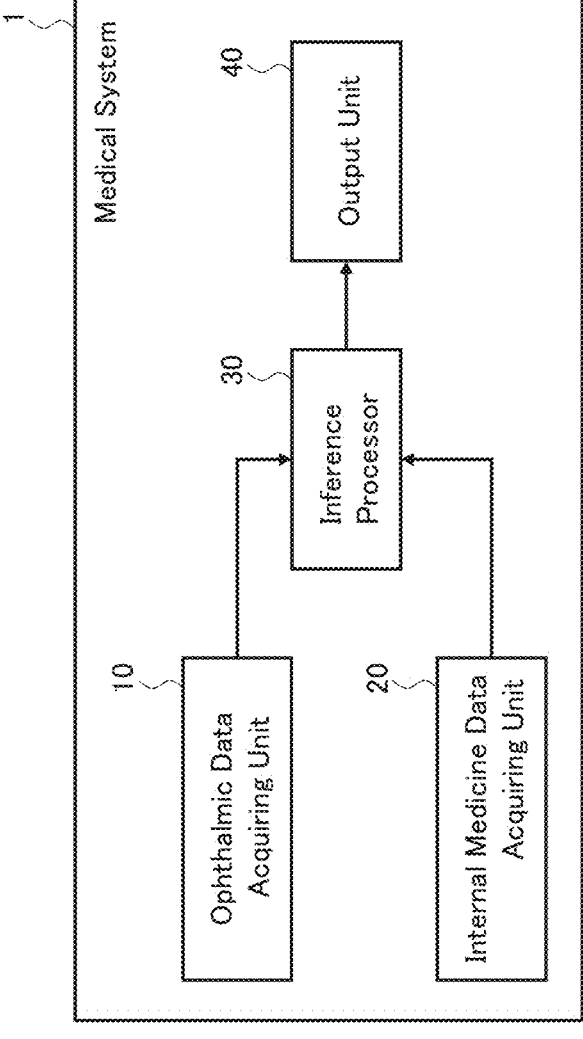
FIG. 1 is a diagram illustrating an example of a configuration of a medical system according to an aspect example.

The present disclosure provides descriptions of several aspect examples of a medical system. A medical system of an aspect example is configured to execute, by using a computer, diagnostic inference based on ophthalmic data and internal medicine data both obtained from a patient. This computer of some typical examples includes a learning model constructed by machine learning. Ophthalmic data includes data acquired from a patient's eye using an examination apparatus (ophthalmic examination apparatus) that is (mainly) used in the field of ophthalmology. Internal medicine data includes data acquired from a patient using an examination apparatus (internal medicine examination apparatus) that is (mainly) used in the field of internal medicine. Internal medicine data may include any of electronic medical record data, clinical encounter (patient encounter, medical interview) data, and patient's background information (e.g., age, treatment history, medical history, health history, medication history, surgical history, etc.).

A medical system of an aspect example is capable of detecting complex physiological events such as symptoms of a disease and signs of aggravation of a disease with high precision by performing comprehensive processing of ophthalmic data and internal medicine data. In addition to this, a medical system of some aspect examples is devised by taking the background described below into account, and can achieve corresponding advantageous effects.

Healthcare workers such as doctors and nurses are exposed to the risk of in-hospital infection (healthcare-associated infection). For example, during the pandemic of the novel coronavirus infection (Coronavirus Disease 2019; COVID-19) in 2020, the risk of infection to healthcare workers became one of major problems, as cluster infections occurred at medical institutions that were crowded with patients. The increased risk of infection to healthcare workers can occur not only during epidemics of infectious diseases, but also in the event of disasters or major accidents.

In general, it is considered important to ensure a sufficient distance between people (what is referred to as social distancing) to reduce the risk of infection. However, it is not easy to keep adequate social distances in standard clinical environment. For example, when using a stethoscope to listen to sounds generated by a heart, lungs, blood vessels, and so forth, or when using a slit lamp microscope to observe an eye, the doctor or other healthcare workers must be in close proximity to the patient to carry out the procedure.

A medical system of some aspect examples is configured to provide a result of diagnostic inference on the basis of both data acquired from an ophthalmic examination apparatus and data acquired from an internal medicine examination apparatus, to a doctor's computer terminal that is located remotely from both the ophthalmic examination apparatus and the internal medicine examination apparatus. This medical system makes it possible to realize utilization, for a diagnostic purpose, of data acquired from examinations (e.g., auscultation, slit lamp examination, etc.) that could not previously be performed without being in close proximity to a patient. In other words, according to the medical system of some aspect examples, it becomes possible to maintain social distances between patients and healthcare workers, and also to achieve detection of complex physiological events, such as disease symptoms and aggravation signs, with high precision.

Here, being "located remotely" may be any positional relationship that can keep social distances between patients and healthcare workers. For example, the doctor's computer terminal may be located in a room separate from a room in which the examination apparatus is located, or may be located in a facility separate from a facility in which the examination apparatus is located.

It should be noted that in the cases where an examination is conducted under an adequate infection protection system, such as when full protective clothing is worn, it is not necessary to ensure social distancing. In the cases where only some of the examinations (referred to as specific examinations) are conducted under an adequate infection protection system, the medical system may be configured to provide information to a doctor's computer terminal located remotely from each of the examination apparatuses used for examinations other than the specific examinations.

Any of the aspect examples in the present disclosure may be modified by any of the matters and items described in the documents cited herein and any other known techniques or technologies. This modification may be, for example, any of addition, combination, substitution, replacement, deletion, omission, and other processing.

At least one or more of the functions of the elements described in the present disclosure may be implemented by using a circuit configuration (circuitry) or a processing circuit configuration (processing circuitry). The circuitry or the processing circuitry may include any of the followings, all of which are configured and/or programmed to execute at least one or more functions disclosed herein: a general purpose processor, a dedicated processor, an integrated circuit, a central processing unit (CPU), a graphics processing unit (GPU), an application specific integrated circuit (ASIC), a programmable logic device (e.g., a simple programmable logic device (SPLD), a complex programmable logic device (CPLD), or a field programmable gate array (FPGA)), an existing or conventional circuit configuration or circuitry, and any combination of these. A processor may be considered to be processing circuitry or circuitry that includes a transistor and/or another circuitry. In the present disclosure, circuitry, a circuit, a computer, a processor, a unit, a means, a part, a section, or a term similar to these may include hardware that executes at least one or more functions disclosed herein, and/or hardware that is programmed to execute at least one or more functions disclosed herein. Hardware may be the hardware disclosed herein, or alternatively, known hardware that is programmed and/or configured to execute at least one or more functions described herein. In the case in which the hardware is a processor, which may be considered as a certain type of circuitry, then circuitry, a circuit, a computer, a processor, a unit, a means, a part, a section, or a term similar to these may be a combination of hardware and software. In this case, the software may be used to configure the hardware and/or the processor.

The aspect examples described below may be freely combined. For example, two or more of the aspect examples may be combined at least in part.

<System Configuration>

Several examples of a configuration of a medical system of some aspect examples will be described. The medical system 1 illustrated in FIG. 1 includes the ophthalmic data acquiring unit 10, the internal medicine data acquiring unit 20, the inference processor 30, and the output unit 40. In some typical examples, the inference processor 30 is connected to both the ophthalmic data acquiring unit 10 and the internal medicine data acquiring unit 20 via a communication line. This communication line may form a network in a medical institution, or may form a network across a plurality of facilities. The communication technology applied to this communication line may be freely determined, and may include any of various kinds of known communication technologies such as wired communication, wireless communication, near field communication, and so forth.

The ophthalmic data acquiring unit 10 is configured to acquire ophthalmic data from a patient and includes at least one ophthalmic examination apparatus. An ophthalmic examination apparatus is an apparatus used for an examination of an eye (ophthalmic examination). Ophthalmic data acquired by the ophthalmic data acquiring unit 10 is sent to the inference processor 30 through the communication line. Types of the ophthalmic examination apparatus include an ophthalmic measurement apparatus and an ophthalmic imaging apparatus.

The ophthalmic measurement apparatus is an apparatus for acquiring ocular characteristic data. Ocular characteristic data is data representing a condition of an eye, and is characteristic data such as numerical data, evaluation data, or the like. Types of the ophthalmic measurement apparatus include an ocular blood flow measurement apparatus, an ocular refraction measurement apparatus, a tonometer, a corneal endothelial cell examination apparatus (a specular microscope), a higher order aberration measurement apparatus (a wavefront analyzer), a visual acuity test apparatus, a perimeter, a microperimeter, an ocular axial length measurement apparatus, an electroretinography apparatus, a binocular visual function examination apparatus, a color vision examination apparatus, and so forth.

The ocular blood flow measurement apparatus may be, for example, an optical coherence tomography (OCT) apparatus described in Japanese Unexamined Patent Application Publication No. 2020-48730, or a laser speckle flowgraphy (LSFG) apparatus described in Japanese Unexamined Patent Application Publication (Translation of PCT Application) No. 2017-504836.

Japanese Unexamined Patent Application Publication No. 2018-38518 discloses an example of the ocular refraction measurement apparatus (a refractometer, a keratometer), an example of the tonometer (a non-contact tonometer), an example of the specular microscope, and an example of the wavefront analyzer.

The visual acuity test apparatus may be, for example, an apparatus capable of conducting remote visual acuity tests described in Japanese Unexamined Patent Application Publication No. 2018-110687.

Any known apparatuses may be employed for other types of ophthalmic measurement apparatuses.

The ophthalmic imaging apparatus is an apparatus for acquiring ocular image data from a patient. Ocular image data is visual data (visualization) obtained by any ophthalmic modality. This ophthalmic modality may be, for example, a photographing type modality or a scanning type modality. Types of the ophthalmic imaging apparatus include an optical coherence tomography apparatus, a fundus camera, a slit lamp microscope, and a surgical microscope.

The optical coherence tomography apparatus and the fundus camera may be, for example, apparatuses in which various kinds of imaging preparation operations are automated, as described in Japanese Unexamined Patent Application Publication No. 2020-44027. Note that the imaging preparation operations are performed to prepare imaging conditions. Examples of the imaging preparation operations include alignment adjustment, focus adjustment (focusing), optical path length adjustment, polarization adjustment, and light amount adjustment. Further, the optical coherence tomography apparatus and the fundus camera may be configured to perform an automatic operation for maintaining favorable imaging conditions achieved by the imaging preparation operations. Examples of the automatic operation include automatic alignment adjustment in accordance with an eye movement (eye tracking), automatic optical path length adjustment in accordance with an eye movement (Z lock), and so forth.

A slit lamp microscope may be, for example, an apparatus usable for remote imaging, as that described in Japanese Unexamined Patent Application Publication No. 2019-213734.

A surgical microscope may be, for example, an apparatus usable for remote surgery, as that described in Japanese Unexamined Patent Application Publication No. 2002-153487.

Any known apparatuses may be employed for other types of ophthalmic imaging apparatuses.

An ophthalmic examination apparatus of some typical examples may be configured to be capable of performing remote operation and remote control, as the inventions described in the documents mentioned above. As an example, considering the risk of infection to healthcare workers, separate rooms for examination and operation can be prepared as an examination room and an operation room. Here, the examination room is used for conducting an examination using an ophthalmic examination apparatus, and the operation room is used for performing an operation of the ophthalmic examination apparatus. In addition to the ophthalmic examination apparatus, the examination room may be equipped with the followings: a speaker and/or a display to output an instruction issued by an operator from the operation room (e.g., output voice, image, video, etc.), a video camera to photograph a subject (patient) in the examination room, a microphone to input voice of the subject, and a computer connected to the ophthalmic examination apparatus. On the other hand, the operation room is equipped with the followings: a device, such as a computer and/or an operation panel, used for remote operation of the ophthalmic examination apparatus, a display that displays data acquired by the ophthalmic examination apparatus (e.g., a display connected to the computer in the examination room), a video camera and/or a microphone to input an instruction for the subject, and a computer connected to the ophthalmic examination apparatus. With such configurations, the operator can conduct remote operation, from the operation room, of the ophthalmic examination apparatus located in the examination room using an application programming interface (API), for example. The operator can also send an instruction from the operation room to the subject by the use of a videophone. Therefore, it becomes possible to significantly reduce the risk of the operator, who is a healthcare worker, getting an infection from the subject.

Figure 2A:
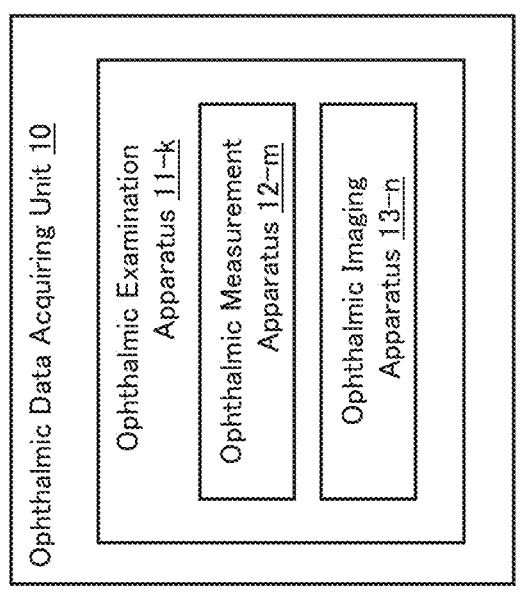
FIG. 2A is a diagram illustrating an example of a configuration of a medical system according to an aspect example.
Figure 2B:
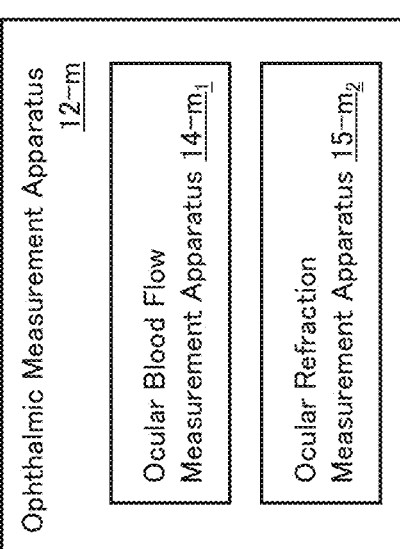
FIG. 2B is a diagram illustrating an example of a configuration of a medical system according to an aspect example.

A configuration example of the ophthalmic data acquiring unit 10 is shown in FIG. 2A and FIG. 2B. The ophthalmic data acquiring unit 10 shown in FIG. 2A is provided with the K number of ophthalmic examination apparatuses 11-$k$. Here, the number K is an integer equal to or greater than 1 (K≥1), and the number k is an integer that belongs to the range of 1 to K (1≤k≤K). The K number of ophthalmic examination apparatuses 11-$k$ include the M number of ophthalmic measurement apparatuses 12-$m$ and the N number of ophthalmic imaging apparatuses 13-$n$. Here, the sum of the number M and the number N is equal to the number K (M+N=K), the number M is an integer equal to or greater than 0 (M≥0), the number m is an integer that belongs to the range of 0 to M (0≤m≤M), the number N is an integer equal to or greater than 0 (N≥0), and the number n is an integer that belongs to the range of 0 to N (0≤n≤N).

In the example shown in FIG. 2B, the number M, which is the number of the ophthalmic measurement apparatuses 12-$m$, is an integer equal to or greater than 1 (M≥1). The M number of ophthalmic measurement apparatuses 12-$m$ include the $M_1$ number of ocular blood flow measurement apparatuses 14-$m_1$ and the $M_2$ number of ocular refraction measurement apparatuses 15-$m_2$. Here, the sum of the number $M_1$ and the number $M_2$ is equal to the number M ($M_1+M_2$=M), the number $M_1$ is an integer equal to or greater than 0 ($M_1$≥0), the number $m_1$ is an integer that belongs to the range of 0 to $M_1$ (0≤$m_1$≤$M_1$), the number $M_2$ is an integer equal to or greater than 0 ($M_2$≥0), and the number $m_2$ is an integer that belongs to the range of 0 to $M_2$ (0≤$m_2$≤$M_2$).

The internal medicine data acquiring unit 20 is configured to acquire internal medicine data from a patient and includes at least one internal medicine examination apparatus. The internal medicine examination apparatus is an apparatus used (mainly) in the field of internal medicine. Internal medicine data acquired by the internal medicine data acquiring unit 20 is sent to the inference processor 30 through the communication line. There are various types of internal medicine examination apparatuses, some of which are illustrated in FIG. 3.

Figure 3:
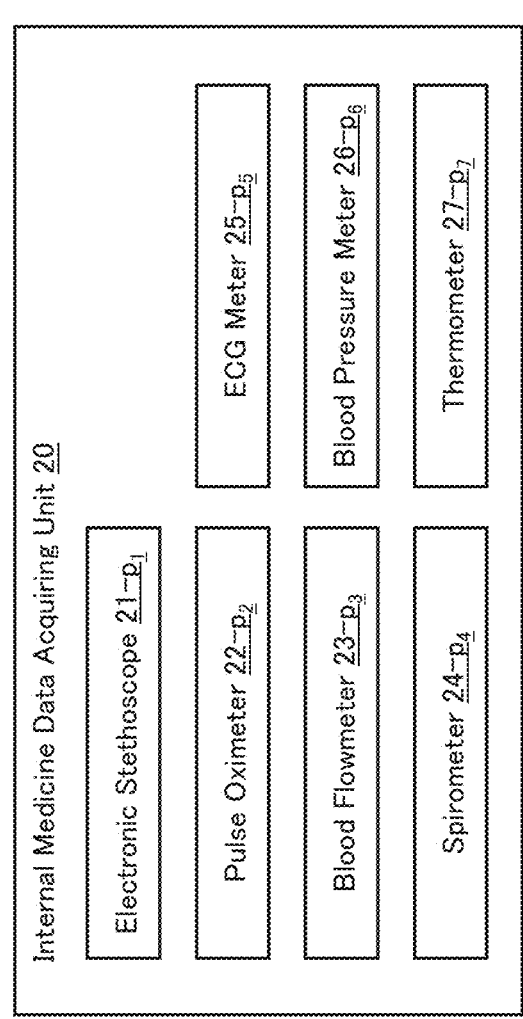
FIG. 3 is a diagram illustrating an example of a configuration of a medical system according to an aspect example.

An example of the internal medicine data acquiring unit 20 shown in FIG. 3 includes the electronic stethoscope 21-$p_1$, the pulse oximeter 22-$p_2$, the blood flowmeter 23-$p_3$, the spirometer 24-$p_4$, the electrocardiogram meter 25-$p_5$, the blood pressure meter 26-$p_6$, and the thermometer 27-$p_7$. Here, each of the numbers $p_1$ to $p_7$ is an integer equal to or greater than 0 ($p_1$, . . . , $p_7$≥0), and the sum of the numbers $p_1$ to $p_7$ is an integer equal to or greater than 1 ($p_1$+ . . . +$p_7$≥1).

The electronic stethoscope 21-$p_1$ is a device for acquiring auscultatory sound data (auscultation data, auscultation sound data, auscultatory data), and may be, for example, the device described in Japanese Unexamined Patent Application Publication No. 2017-198. Types of auscultatory sound detected by the use of the electronic stethoscope 21-$p_1$ may be freely determined, and may be, for example, at least one of: tracheal breath sounds, bronchial breath sounds, alveolar breath sounds, heart sounds, and blood flow sounds.

The pulse oximeter 22-$p_2$ is a device for acquiring blood oxygen saturation data (blood oxygen data, blood oxygenation data), and may be, for example, the pulse oximeter described in Japanese Unexamined Patent Application Publication No. 2019-111010. Types of blood oxygen saturation data detected by the use of the pulse oximeter 22-$p_2$ may be freely determined, and may be, for example, at least one of: oxygen saturation, oxygen content, and oxygen supply (feed rate).

The blood flowmeter 23-$p_3$ is a device for acquiring blood flow data and/or pulse data (pulse rate data), and may be any of the following devices: the ultrasonic blood flowmeter described in Japanese Unexamined Patent Application Publication No. 2008-36095, the laser blood flowmeter described in Japanese Unexamined Patent Application Publication No. 2008-154804, and the electromagnetic blood flowmeter described in Japanese Unexamined Patent Application Publication No. Hei10-328152. Types of blood flow data detected by the use of the blood flowmeter 23-$p_3$ may be freely determined, and may be, for example, at least one of: blood flow velocity, blood flow rate, and blood flow velocity distribution.

The spirometer 24-$p_4$ is a device for acquiring respiratory function data, and may be, for example, the respiratory monitoring system described in Japanese Unexamined Patent Application Publication (Translation of PCT Application) No. 2019-527117. Types of respiratory function data detected by the use of the spirometer 24-$p_4$ may be freely determined, and may be, for example, at least one of: respiratory rate, tidal volume, minute ventilation (pulmonary ventilation per minute, minute volume (MV), minute breathing capacity (MBC)), intratracheal pressure, airflow velocity and amount, ventilation work amount, inspiratory gas concentration, and inspiratory water vapor.

The electrocardiogram meter 25-$p_5$ is a device for acquiring either one of or both electrocardiogram data and heart rate data, and may be, for example, the heart rate and electrocardiogram meter described in Japanese Unexamined Patent Application Publication No. 2017-148577. The data detected by the use of the electrocardiogram meter 25-$p_5$ may be, for example, either one of or both electrocardiographic waveform and heart rate.

The blood pressure meter 26-$p_6$ is a device for acquiring either one of or both blood pressure data and pulse data, and may be, for example, the blood pressure meter in the system described in Japanese Unexamined Patent Application Publication No. 2018-29964. The data detected by the use of the blood pressure meter 26-$p_6$ may be, for example, either one of or both blood pressure and pulse rate.

The thermometer 27-$p_7$ is a device for acquiring body temperature data, and may be, for example, the thermometer in the system described in Japanese Unexamined Patent Application Publication No. 2018-29964.

The inference processor 30 is configured to execute inference processing using a trained model. The trained model has been constructed by machine learning using training data. This training data includes clinical data.

For example, the clinical data included in the training data includes clinically collected ophthalmic data, clinically collected internal medicine data, and clinically collected diagnostic result data. In some typical examples, a set of ophthalmic data, internal medicine data, and diagnostic result data is associated with a corresponding clinical case or a corresponding patient, and diagnostic result data is obtained by a doctor or another inference model (another trained model) based on corresponding ophthalmic data and corresponding internal medicine data.

Through machine learning (supervised learning) executed on the basis of such training data, a trained model (inference model) is created that is configured to receive as an input both ophthalmic data acquired from a patient by the ophthalmic data acquiring unit 10 and internal medicine data acquired from this patient by the internal medicine data acquiring unit 20 and to output an inferred diagnostic result (inferred diagnostic data).

The inference processor 30 includes the trained model thus obtained, and is configured to input both ophthalmic data acquired from a patient by the ophthalmic data acquiring unit 10 and internal medicine data acquired from this patient by the internal medicine data acquiring unit 20 into the trained model, and to transmit inferred diagnostic data output from the trained model to the output unit 40.

Machine learning algorithms that can be used for some aspect examples are not limited to supervised learning, and may be any types of algorithms such as unsupervised learning, semi-supervised learning, reinforcement learning, transduction, and multi-task learning. A combination of any two or more algorithms may also be employed.

Methods and techniques of machine learning that can be used for some aspect examples may be freely selected, and may be any methods and techniques such as neural network, support vector machine, decision tree learning, association rule learning, genetic programming, clustering, Bayesian network, feature learning, representation learning, and extreme learning machine. A combination of any two or more methods and techniques may also be employed.

Figure 4:
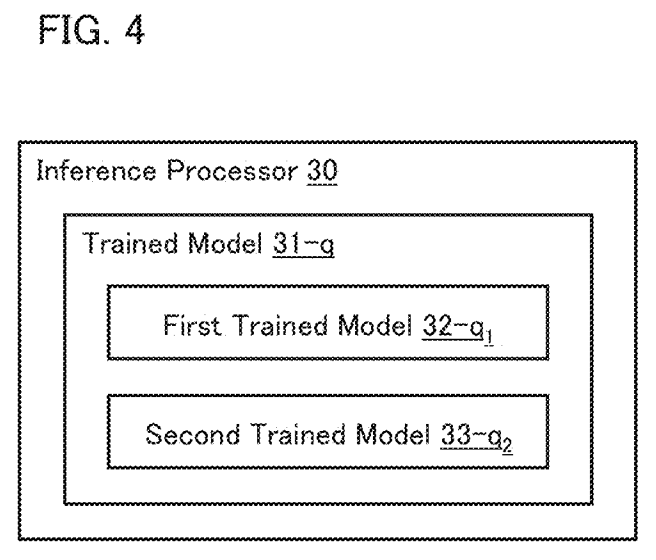

A configuration example of the inference processor 30 is shown in FIG. 4. The example of the inference processor 30 shown in FIG. 4 includes the Q number of trained models 31-$q$. Here, the number Q is an integer equal to or greater than 1 (Q1), and the number q is an integer that belongs to the range of 1 to Q. The trained model 31-$q$ includes the $Q_1$ number of first trained models 32-$q_1$ and the $Q_2$ number of second trained models 33-$q_2$. Here, the sum of the number $Q_1$ and the number $Q_2$ is equal to the number Q ($Q_1+Q_2=Q$), the number $Q_1$ is an integer equal to or greater than 0 ($Q_1 \geq 0$), the number $q_1$ is an integer that belongs to the range of 0 to $Q_1$ ($0 \leq q_1 \leq Q_1$), the number $Q_2$ is an integer equal to or greater than 0 ($Q_2 \geq 0$), and the number $q_2$ is an integer that belongs to the range of 0 to $Q_2$ ($0 \leq q_2 \leq Q_2$).

The first trained model 32-$q_1$ is constructed by machine learning using training data that includes either one of or both ocular characteristic data and ocular image data, and also includes diagnostic result data. For example, the ocular characteristic data and/or the ocular image data are both collected clinically. Typically, a set of ocular characteristic data and/or ocular image data as well as diagnostic result data is associated on a corresponding clinical case or a corresponding patient, and diagnostic result data is obtained by a doctor or another inference model based on corresponding ocular characteristic data and/or corresponding ocular image data.

Through machine learning (supervised learning) executed on the basis of such training data, a trained model (inference model) is created that is configured to receive as an input either one of or both ophthalmic characteristic data from a patient by the ophthalmic measurement apparatus 12-$m$ of the ophthalmic data acquiring unit 10 and ophthalmic image data acquired from this patient by the ophthalmic imaging apparatus 13-$n$ of the ophthalmic data acquiring unit 10 and to output an inferred diagnostic result (inferred diagnostic data).

The training data used to construct the first trained model 32-$q_1$ may include either one of or both ocular characteristic data and ocular image data, internal medicine data, and diagnostic result data. In other words, the training data used to construct the first trained model 32-$q_1$ may further include internal medicine data. If this is the case, a trained model (inference model) is created that is configured to receive as an input either one of or both ophthalmic characteristic data acquired from a patient by the ophthalmic measurement apparatus 12-$m$ of the ophthalmic data acquiring unit 10 and ophthalmic image data acquired from this patient by the ophthalmic imaging apparatus 13-$n$, and internal medicine data acquired by the internal medicine data acquiring unit 20, and to output an inferred diagnostic result (inferred diagnostic data).

The second trained model 33-$q_2$ is constructed by machine learning using training data that includes internal medicine data and diagnostic result data. The internal medicine data is, for example, at least one of: auscultatory sound data, blood flow data, pulse data, respiratory function data, electrocardiogram data, heart rate data, blood pressure data, and body temperature data. The internal medicine data is collected clinically. In some typical examples, internal medicine data and diagnostic result data are both associated with a corresponding clinical case or a corresponding patient, and diagnostic result data is obtained by a doctor or another inference model based on corresponding internal medicine data.

Through machine learning (supervised learning) executed on the basis of such training data, a trained model (inference model) is created that is configured to receive as an input internal medicine data acquired from a patient by the internal medicine data acquiring unit 20 and to output an inferred diagnostic result (inferred diagnostic data).

The training data used to construct the second trained model 33-$q_2$ may include internal medicine data, ophthalmic data, and diagnostic result data. In other words, the training data used to construct the second trained model 33-$q_2$ may further include ophthalmic data. If this is the case, a trained model (inference model) is created that is configured to receive as an input both ophthalmic data acquired by the ophthalmic data acquiring unit 10 and internal medicine data acquired by the internal medicine data acquiring unit 20, and to output an inferred diagnostic result (inferred diagnostic data).

In the case where the trained model 31-$q$ includes one or more of the first trained model 32-$q_1$ and one or more of the second trained model 33-$q_2$ ($Q_1 \geq 1$ and $Q_2 \geq 1$), any types of the data listed below is input, for example, into the trained model 31-$q$: (1A) ocular characteristic data acquired from a patient by the ophthalmic measurement apparatus 12-$m$, (1B) ocular image data acquired from the patient by the ophthalmic imaging apparatus 13-$n$, (2A) auscultatory sound data acquired from the patient by the electronic stethoscope 21-$p_1$, (2B) blood oxygen saturation data acquired from the patient by the pulse oximeter 22-$p_2$, (2C) either one of or both blood flow data and pulse data acquired from the patient by the blood flowmeter $23\text{-}p_3$, (2D) respiratory function data acquired from the patient by the spirometer $24\text{-}p_4$, (2E) either one of or both electrocardiogram data and heart rate data acquired from the patient by the electrocardiogram meter $25\text{-}p_5$, (2F) either one of or both blood pressure data and pulse data acquired from the patient by the blood pressure meter $26\text{-}p_6$, and (2G) body temperature data acquired from the patient by the thermometer $27\text{-}p_7$.

In the case where the ocular characteristic data (1A) and/or the ocular image data (1B) are/is input into the trained model $31\text{-}q$, the ocular characteristic data (1A) and/or the ocular image data (1B) are/is then input at least into the first trained model $32\text{-}q_1$. The first trained model $32\text{-}q_1$ performs inference processing based on the ocular characteristic data (1A) and/or the ocular image data (1B) to output inferred diagnostic data.

In the case where any one or more types of the internal medicine data (2A) to (2G) is input into the trained model $31\text{-}q$, the one or more types of the internal medicine data (2A) to (2G) is then input at least into the second trained model $33\text{-}q_2$. The second trained model $33\text{-}q_2$ performs inference processing based on the one or more of the input internal medicine data (2A) to (2G) to output inferred diagnostic data.

As a result, the inferred diagnostic data as an output from the first trained model $32\text{-}q_1$ and the inferred diagnostic data as an output from the second trained model $33\text{-}q_2$ are both obtained. The inference processor 30 may generate final inferred diagnostic data (inferred diagnostic data as an output from the inference processor 30) based on a plurality of pieces of inferred diagnostic data obtained in this way. In some examples, the inference processor 30 may select any one or more from the plurality of pieces of inferred diagnostic data. For example, the inference processor 30 may select inferred diagnostic data with the highest confidence. Alternatively, the inference processor 30 may generate final inferred diagnostic data by combining two or more of the plurality of pieces of inferred diagnostic data. As another alternative, the inference processor 30 may generate final inferred diagnostic data that includes two or more of the plurality of pieces of inferred diagnostic data (e.g., final inferred diagnostic data that includes a list of two or more of the plurality of pieces of inferred diagnostic data).

In the case where the ocular characteristic data (1A) and/or the ocular image data (1B) are/is input into the trained model $31\text{-}q$, the ocular characteristic data (1A) and/or the ocular image data (1B) may be then input into the second trained model $33\text{-}q_2$. If this is the case, the second trained model $33\text{-}q_2$ performs inference processing based not only on the ocular characteristic data (1A) and/or the ocular image data (1B) but also on one or more of the plurality of pieces of internal medicine data (2A) to (2G), thereby outputting inferred diagnostic data.

Similarly, in the case where any one or more of the plurality of pieces of internal medicine data (2A) to (2G) are input into the trained model $31\text{-}q$, the one or more of the plurality of pieces of internal medicine data (2A) to (2G) is then input at least into the first trained model $32\text{-}q_1$. If this is the case, the first trained model $32\text{-}q_1$ performs inference processing based not only on the one or more of the plurality of pieces of internal medicine data (2A) to (2G) but also on the ocular characteristic data (1A) and/or the ocular image data (1B), thereby outputting inferred diagnostic data.

The item (e.g., disease, symptom, etc.) on which inference processing is executed by the inference processor 30 may be freely selected. For example, the inference processor 30 may be configured to perform inference processing regarding pneumonia. More specifically, the inference processor 30 may be configured to perform any of the following types of inference processing: inference processing for calculating a probability that a patient has pneumonia (pneumonia contraction probability), inference processing for calculating a probability that a patient has an infectious disease associated with pneumonia (infectious disease contraction probability), inference processing for determining a severity of pneumonia in a patient (pneumonia severity), and inference processing for determining a severity of infectious disease associated with pneumonia in the patient (infectious disease severity).

In the case of obtaining a pneumonia contraction probability, the trained model $31\text{-}q$ of the inference processor 30 is constructed by machine learning based on training data that includes ophthalmic data, internal medicine data, and diagnostic result data representing pneumonia contraction state (pneumonia contraction condition, presence or absence of pneumonia). Furthermore, ophthalmic data acquired from a patient by the ophthalmic data acquiring unit 10 and internal medicine data acquired from this patient by the internal medicine data acquiring unit 20 are input into the trained model $31\text{-}q$, and inferred diagnostic data including a pneumonia contraction probability for this patient is output from the trained model $31\text{-}q$.

In the case of obtaining a pneumonia contraction probability, the trained model $31\text{-}q$ of the inference processor 30 is constructed by machine learning based on training data that includes ophthalmic data, internal medicine data, and diagnostic result data representing pneumonia contraction state (pneumonia contraction condition, presence or absence of pneumonia). Furthermore, ophthalmic data acquired from a patient by the ophthalmic data acquiring unit 10 and internal medicine data acquired from this patient by the internal medicine data acquiring unit 20 are input into the trained model $31\text{-}q$, and inferred diagnostic data including a pneumonia contraction probability for this patient is output from the trained model $31\text{-}q$.

In the case of obtaining an infectious disease contraction probability, the trained model $31\text{-}q$ of the inference processor 30 is constructed by machine learning based on training data that includes ophthalmic data, internal medicine data, and diagnostic result data representing a contraction state (contraction condition) of a target infectious disease (presence or absence of a target infectious disease). Furthermore, ophthalmic data acquired from a patient by the ophthalmic data acquiring unit 10 and internal medicine data acquired from this patient by the internal medicine data acquiring unit 20 are input into the trained model $31\text{-}q$, and inferred diagnostic data including an infectious disease contraction probability for this patient is output from the trained model $31\text{-}q$.

In the case of obtaining a pneumonia severity, the trained model $31\text{-}q$ of the inference processor 30 is constructed by machine learning based on training data that includes ophthalmic data, internal medicine data, and diagnostic result data representing the state or condition of pneumonia such as severity and/or information on severity. Furthermore, ophthalmic data acquired from a patient by the ophthalmic data acquiring unit 10 and internal medicine data acquired from this patient by the internal medicine data acquiring unit 20 are input into the trained model $31\text{-}q$, and inferred diagnostic data including a pneumonia severity for this patient is output from the trained model $31\text{-}q$.

In the case of obtaining an infectious disease severity, the trained model $31\text{-}q$ of the inference processor 30 is constructed by machine learning based on training data that includes ophthalmic data, internal medicine data, and diagnostic result data representing the state or condition of a target infectious disease such as severity and/or information on severity. Furthermore, ophthalmic data acquired from a patient by the ophthalmic data acquiring unit 10 and internal medicine data acquired from this patient by the internal medicine data acquiring unit 20 are input into the trained model 31-*q*, and inferred diagnostic data including an infectious disease severity for this patient is output from the trained model 31-*q*.

The infectious disease associated with pneumonia may be, for example, novel coronavirus infection (COVID-19). Further, the severity of the infectious disease associated with pneumonia may be related to freely selected symptoms such as cytokine storm, fever, conjunctival hyperemia (conjunctival congestion), nasal congestion, headache, cough, sore throat, sputum, bloody sputum, malaise, fatigue, shortness of breath, nausea, vomiting, diarrhea, myalgia, joint pain, chills, and so forth. In addition, the severity of the infectious disease associated with pneumonia may be related to any underlying medical conditions, application of dialysis, administration of specific medications, and so forth. Examples of the underlying medical conditions include diabetes, heart failure, and respiratory diseases such as chronic obstructive pulmonary disease (COPD). Examples of the specific medications include immunosuppressants (immunosuppressive drugs, immunosuppressive agents), and anticancer drugs.

The output unit 40 outputs a result of the inference processing performed by the inference processor 30. The mode or aspect of output processing may be freely selected, and may be any of transmission, display, recording, and printing. Information output by the output unit 40 may be the result of the inference processing itself (inferred diagnostic data), information including the result of the inference processing, or information obtained by applying further processing to the result of the inference processing. For example, the medical system 1 may further include a report creating unit (not shown in the drawings) configured to generate a report based on inferred diagnostic data obtained by the inference processor 30. If this is the case, the output unit 40 may output the report generated in this way.

Figure 5:
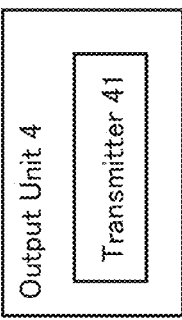
FIG. 5 is a diagram illustrating an example of a configuration of a medical system according to an aspect example.

A configuration example of the output unit 40 is shown in FIG. 5. The example of the output unit 40 shown in FIG. 5 includes the transmitter 41. The transmitter 41 is configured to transmit a result of the inference processing performed by the inference processor 30 to a doctor's computer terminal that is located remotely from both the ophthalmic data acquiring unit 10 and the internal medicine data acquiring unit 20.

Here, the transmission from the output unit 40 to the doctor's computer terminal may be direct transmission or indirect transmission. The direct transmission is a mode or aspect of transmitting a result of the inference processing (e.g., inferred diagnostic data, a report, etc.) from the output unit 40 to the doctor's computer terminal. On the other hand, the indirect transmission is a mode or aspect of transmitting a result of the inference processing to an apparatus or device (e.g., a server, a database, etc.) other than the doctor's computer terminal and then providing the result of the inference processing to the doctor's computer terminal from this apparatus or device.

By employing the configuration, as described thus far, in which the doctor's computer terminal is placed at a remote location from both the ophthalmic data acquiring unit 10 and the internal medicine data acquiring unit 20, and in which inferred diagnostic data (or information generated from inferred diagnostic data) generated by the inference processor 30 based on ophthalmic data acquired from a patient by the ophthalmic data acquiring unit 10 and internal medicine data acquired from this patient by the internal medicine data acquiring unit 20 is provided to the doctor's computer terminal, social distance between the doctor (healthcare worker) and the patient can be maintained, and therefore the risk of infection to the doctor (healthcare worker) can be reduced.

<Usage Mode of the System>

Figure 6:
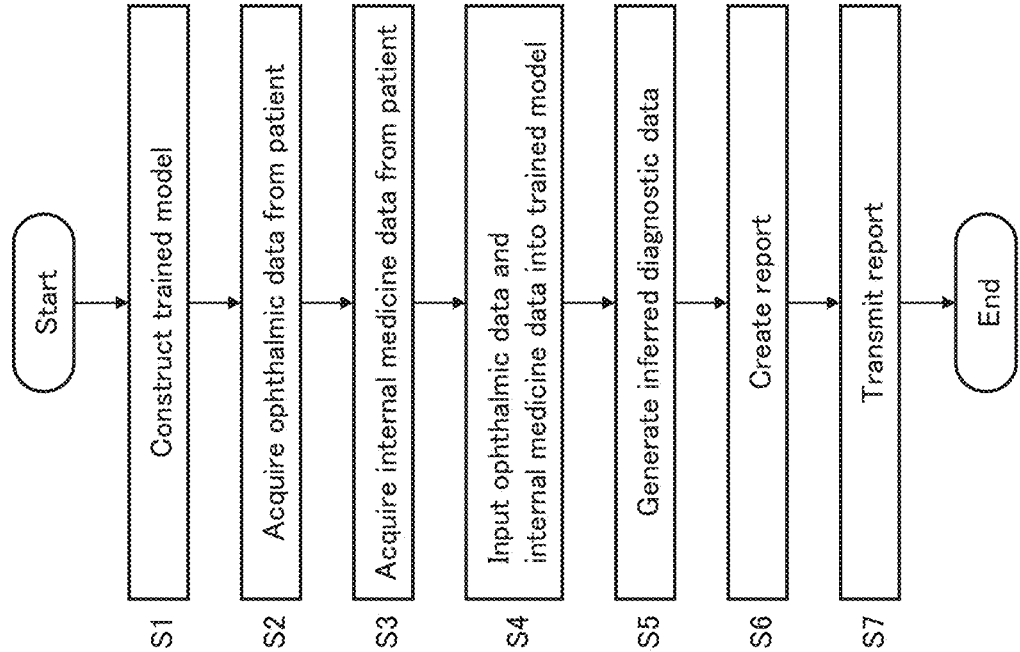
FIG. 6 is a flowchart illustrating an example of an operation of a medical system according to an aspect example.

An example of a usage mode of the medical system 1 according to the present aspect example will be described with reference to the flowchart of FIG. 6.

(S1: Construct Trained Model)

In preparation for putting the medical system 1 into implementation, a trained model 31-*q* to be used in the inference processor 30 is constructed. Note that processing performed at this stage may be updating of a trained model that has already been used, that is, adjustment or updating of parameters in a trained model that has already been used.

(S2: Acquire Ophthalmic Data from Patient)

A subject may be, for example, a patient with a confirmed diagnosis (definitive diagnosis) of novel coronavirus infection (COVID-19) or a patient with suspected novel coronavirus infection (COVID-19). The ophthalmic data acquiring unit 10 of the medical system 1 acquires ophthalmic data of a predetermined item from the patient.

(S3: Acquire Internal Medicine Data from Patient)

Further, the internal medicine data acquiring unit 20 of the medical system 1 acquires internal medicine data of a predetermined item from the patient.

The relationship between the timing of acquiring ophthalmic data and the timing of acquiring internal medicine data may be freely determined. For example, internal medicine data may be acquired after acquisition of ophthalmic data, ophthalmic data may be acquired after acquisition of internal medicine data, or ophthalmic data and internal medicine data may be acquired in parallel or simultaneously.

In addition, the time difference between ophthalmic data acquisition and internal medicine data acquisition may also be freely determined. For example, in the case where fundus blood flow data is acquired as ophthalmic data and heart rate data is acquired as internal medicine data, since there is a time lag between fundus blood flow data and heart rate data, there is no need to acquire both fundus blood flow data and heart rate data at the same time, and about 10 minutes of time difference between their acquisitions may be allowed, for example. However, it is considered desirable that a condition affecting a blood circulation state, such as posture, be the same between at the time of ophthalmic data acquisition and at the time of internal medicine data acquisition. The same applies for a condition that can affect other examination parameters, such as diet, time slot, drug administration, and so forth.

(S4: Input Ophthalmic Data and Internal Medicine Data into Trained Model)

The ophthalmic data acquired in the step S2 and the internal medicine data acquired in the step S3 are sent to the inference processor 30 and input into the trained model 31-*q*.

(S5: Generate Inferred Diagnostic Data)

The trained model 31-*q* generates inferred diagnostic data from the ophthalmic data and the internal medicine data input in the step S4.

(S6: Create Report)

The medical system 1 (the report creating unit mentioned above, which is not shown in the drawings) creates a report based on the inferred diagnostic data generated in the step S5.

(S7: Transmit Report)

The transmitter 41 of the output unit 40 transmits the report created in the step S6 to a doctor's computer terminal that is located remotely from both the ophthalmic data acquiring unit 10 and the internal medicine data acquiring unit 20. Alternatively, the transmitter 41 of the output unit 40 transmits the report to a computer capable of providing information to the doctor's computer terminal. The doctor's computer terminal is not limited to a computer used by a doctor, and may be a computer used by a healthcare worker other than a doctor (healthcare worker's computer terminal).

According to the medical system 1 described herein, it becomes possible to keep social distances between healthcare workers and patients, and the risks of healthcare workers getting infected from patients can be reduced. Furthermore, since the medical system 1 is configured to automatically perform diagnostic inference based on input including both ophthalmic data and internal medicine data input, disease symptoms and aggravation signs can be detected with higher precision than conventional techniques.

While certain embodiments have been described, these embodiments have been presented by way of example only, and are not intended to limit the scope of the inventions. Indeed, the novel embodiments described herein may be embodied in a variety of other forms; furthermore, various omissions, substitutions, additions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical system comprising:

an ophthalmic data acquiring unit that includes at least one ophthalmic examination apparatus for acquiring ophthalmic data from a patient;

an internal medicine data acquiring unit that includes at least one internal medicine examination apparatus for acquiring internal medicine data from the patient;

an inference processor configured to perform inference processing using a trained model constructed by machine learning using training data that includes ophthalmic data, internal medicine data, and diagnostic result data; and an output unit configured to output a result of the inference processing performed by the inference processor, wherein the inference processor is configured to generate inferred diagnostic data by performing the inference processing based at least on the ophthalmic data of the patient acquired by the ophthalmic data acquiring unit and the internal medicine data of the patient acquired by the internal medicine data acquiring unit, the trained model includes a first trained model and a second trained model, the first trained model being constructed by machine learning using training data that includes diagnostic result data and either one of or both ocular characteristic data and ocular image data, and the second trained model being constructed by machine learning using training data that includes internal medicine data and diagnostic result data, and the inference processor generates the inferred diagnostic data based on an output from the first trained model and an output from the second trained model.

2. The medical system according to claim 1, wherein the at least one ophthalmic examination apparatus includes either one of or both an ophthalmic measurement apparatus for acquiring ocular characteristic data and an ophthalmic imaging apparatus for acquiring ocular image data, and the ophthalmic data to be input into the inference processor includes either one of or both ocular characteristic data acquired from the patient by the ophthalmic measurement apparatus and ocular image data acquired from the patient by the ophthalmic imaging apparatus.

3. The medical system according to claim 2, wherein the ophthalmic measurement apparatus includes either one of or both an ocular blood flow measurement apparatus and an ocular refraction measurement apparatus.

4. The medical system according to claim 3, wherein the ocular blood flow measurement apparatus includes either one of or both an optical coherence tomography apparatus and a laser speckle flowgraphy apparatus.

5. The medical system according to claim 2, wherein the ophthalmic imaging apparatus includes any one or more of an optical coherence tomography apparatus, a fundus camera, a slit lamp microscope, and a surgical microscope.

6. The medical system according to claim 1, wherein the at least one internal medicine examination apparatus includes any one or more of an electronic stethoscope, a pulse oximeter, a blood flowmeter, a spirometer, an electrocardiogram meter, a blood pressure meter, and a thermometer, the electronic stethoscope being for acquiring auscultatory sound data, the pulse oximeter being for acquiring blood oxygen saturation data, the blood flowmeter being for acquiring either one of or both blood flow data and pulse data, the spirometer being for acquiring respiratory function data, the electrocardiogram meter being for acquiring either one of or both electrocardiogram data and heart rate data, the blood pressure meter being for acquiring either one of or both blood pressure data and pulse data, and the thermometer being for acquiring body temperature data, the internal medicine data to be input into the inference processor includes any one or more of: auscultatory sound data acquired from the patient by the electronic stethoscope, blood oxygen saturation data acquired from the patient by the pulse oximeter, either one of or both blood flow data and pulse data acquired from the patient by the blood flowmeter, respiratory function data acquired from the patient by the spirometer, either one of or both electrocardiogram data and heart rate data acquired from the patient by the electrocardiogram meter, either one of or both blood pressure data and pulse data acquired from the patient by the blood pressure meter, and body temperature data acquired from the patient by the thermometer, and the internal medicine data used to train the second trained model are any one or more of auscultatory sound data, blood flow data, pulse data, respiratory function data, electrocardiogram data, heart rate data, blood pressure data, and body temperature data.

7. The medical system according to claim 1, wherein the output unit includes a transmitter configured to transmit a result of the inference processing to a doctor's computer terminal that is located remotely from both the ophthalmic data acquiring unit and the internal medicine data acquiring unit.

8. The medical system according to claim 1, wherein the inference processor performs one or more of: inference processing for calculating a probability that the patient has pneumonia; inference processing for calculating a probability that the patient has an infectious disease associated with pneumonia; inference processing for determining a severity of pneumonia in the patient; and inference processing for determining a severity of an infectious disease associated with pneumonia in the patient.

9. A medical method comprising:

acquiring ophthalmic data from a patient using at least one ophthalmic examination apparatus;

acquiring internal medicine data from the patient using at least one internal medicine examination apparatus;

performing inference processing, using a trained model constructed by machine learning using training data that includes ophthalmic data, internal medicine data, and diagnostic result data, based at least on the ophthalmic data of the patient acquired by the at least one ophthalmic examination apparatus and the internal medicine data of the patient acquired by the at least one internal medicine examination apparatus, thereby generating inferred diagnostic data; and outputting the inferred diagnostic data, wherein the trained model includes a first trained model and a second trained model, the first trained model being constructed by machine learning using training data that includes diagnostic result data and either one of or both ocular characteristic data and ocular image data, and the second trained model being constructed by machine learning using training data that includes internal medicine data and diagnostic result data, and the inference processing is performed to generate the inferred diagnostic data based on an output from the first trained model and an output from the second trained model.

* * * * *